(12) United States Patent
Modiano

(10) Patent No.: US 11,151,858 B2
(45) Date of Patent: Oct. 19, 2021

(54) CROWD MANAGEMENT IN AN ENCLOSED PREMISES

(71) Applicant: Paul Edward Moshe Modiano, Montclair, NJ (US)

(72) Inventor: Paul Edward Moshe Modiano, Montclair, NJ (US)

(*) Notice: Subject to any disclaimer, the term of this patent is extended or adjusted under 35 U.S.C. 154(b) by 0 days.

(21) Appl. No.: 16/945,893

(22) Filed: Aug. 2, 2020

(65) Prior Publication Data

US 2020/0365002 A1  Nov. 19, 2020

Related U.S. Application Data

(60) Provisional application No. 63/043,768, filed on Jun. 24, 2020.

(51) Int. Cl.
| | |
|---|---|
| *G08B 21/04* | (2006.01) |
| *A61B 5/01* | (2006.01) |
| *A61B 5/00* | (2006.01) |
| *G06K 9/00* | (2006.01) |
| *G08B 21/24* | (2006.01) |
| *G08B 3/10* | (2006.01) |
| *G07C 9/10* | (2020.01) |

(52) U.S. Cl.
CPC .......... *G08B 21/0476* (2013.01); *A61B 5/015* (2013.01); *A61B 5/6887* (2013.01); *A61B 5/7405* (2013.01); *G06K 9/00281* (2013.01); *G06K 9/00778* (2013.01); *G07C 9/10* (2020.01); *G08B 3/10* (2013.01); *G08B 21/245* (2013.01)

(58) Field of Classification Search
CPC .............. G08B 21/0476; G08B 21/245; G06K 9/00778; G06K 9/00362; A61B 5/015; G06T 11/60
USPC ........................................................ 340/5.2
See application file for complete search history.

(56) References Cited

U.S. PATENT DOCUMENTS

| | | | | | |
|---|---|---|---|---|---|
| 5,971,605 | A | * | 10/1999 | Aoki ........................ | G07C 9/00 340/545.1 |
| 7,688,349 | B2 | * | 3/2010 | Flickner ............. | G06K 9/00778 348/150 |
| 10,750,953 | B1 | * | 8/2020 | Chase ...................... | A61B 5/01 |
| 2002/0176607 | A1 | * | 11/2002 | Bond ....................... | G07C 9/00 382/107 |
| 2004/0153671 | A1 | * | 8/2004 | Schuyler .................. | G07C 9/00 726/9 |

(Continued)

*Primary Examiner* — Vernal U Brown
(74) *Attorney, Agent, or Firm* — Barry Choobin; Patent 360

(57) ABSTRACT

Disclosed are a system and method for automating crowd management in an enclosed premise. The disclosed system includes an entrance sensor at the entry gate and an exit sensor at the exit gate. The entrance sensor detects entry of a person through the entry gate, while the exit sensor detects exit of a person through the exit. The system further includes a control unit connected to the entrance sensor and the exit sensor. The control unit keeps a tally of persons present inside the enclosed premises at a given time based on the difference between the persons entered and left the enclosed premises. The control unit can analyze the images captured by cameras, installed in the enclosed premises and at the entrance gate, using machine learning algorithms to extract one or more features. The one or more features relates to "the persons wearing the facemask", and "distances between adjacent persons".

13 Claims, 8 Drawing Sheets

(56) References Cited

U.S. PATENT DOCUMENTS

| | | | | |
|---|---|---|---|---|
| 2008/0247609 A1* | 10/2008 | Feris | ................. | G06K 9/00369 |
| | | | | 382/118 |
| 2011/0215932 A1* | 9/2011 | Daniel | ................... | G08B 23/00 |
| | | | | 340/573.1 |
| 2016/0106941 A1* | 4/2016 | Hickey | ................. | A61M 16/06 |
| | | | | 128/203.29 |
| 2017/0220871 A1* | 8/2017 | Ikeda | .................... | G08B 25/00 |

* cited by examiner

CROWD MANAGEMENT IN AN ENCLOSED PREMISES

CROSS-REFERENCE TO RELATED APPLICATIONS

This application claims priority to the U.S. provisional patent application Ser. No. 63/043,768 filed on Jun. 24, 2020, which is incorporated herein by reference in its entirety.

FIELD OF INVENTION

The present invention relates to a system and method for crowd management in an enclosed premises.

BACKGROUND

Retail crowd management is becoming a popular concept in the retail business. It refers to a series of proactive steps taken to regulate the flow of customers in and around a retail store. Retail crowd management becomes particularly important during a sale, such as black Friday sales when large crowds of customers visit the stores for shopping. Retail stores may hire trained staff for managing the crowd at the retail store. The staff members securing the entrance may allow only a limited number of customers to get into the store. For example, at a time, only five customers may enter the store. The number of customers that can enter the store may depend upon the crowd already in the store, and the rate of customers leaving the store. Thus, the staff member at the entrance is typically in regular communication with the staff inside the store for conducting this coordinated activity.

However, crowd management can be an additional burden on the store. The cost of maintaining the staff can be huge, thus may not be feasible for most of the retail stores. Additionally, circumstances, such as an epidemic wherein social distancing between persons is crucial, the physical management by the staff members may not be preferred. The recent SARS Covid-19 infection highlighted the awareness of social distancing during the spread of a contagious disease. A need is, therefore, appreciated for a system and method for automated crowd management in an enclosed premises, such as retail stores.

Herein "enclosed premises" connotes to any enclosed premises having at least one entrance and at least one exit, wherein more than one person can assemble in the enclosed premises for one or more activity. For example, the enclosed premises can be a retails store wherein customer can assemble for shopping.

SUMMARY OF THE INVENTION

The principal object of the present invention is therefore directed to a system and method for automating the crowd management at an enclosed premises.

It is a further object of the present invention that the system and method provide for counting the number of persons in the enclosed premises at a given time.

It is still a further object of the present invention that the system and method can differentiate between a person and the staff.

It is another object of the present invention that the system and method can detect a person not wearing a facemask.

It is another object of the present invention that the system and method can detect a facemask of facemask worn by a person.

It is still another object of the present invention that the system and method can notify the staff about the person not wearing the mask.

It is yet another object of the present invention that the system can control the entry of the persons in the enclosed premises.

It is an additional object of the present invention that the system can determine the number of persons in a queue.

It is a further object of the present invention that the system can determine the approximate waiting time in a queue.

It is still a further object of the present invention that the system can display the waiting time.

It is also an object of the present invention that the system can determine the distances between two or more persons in the enclosed premises.

It is yet a further object of the present invention that the system can determine the distances between persons and the staff members.

It is still an additional object of the present invention that the system can raise an alarm for the persons to maintain the social distancing.

It is yet an additional object of the present invention that the system can track the count of the persons entering and leaving the enclosed premises.

In one aspect, the disclosure herein provides a system for crowd management at an enclosed premises. The system is having an entrance sensor disposed near an entry gate of the enclosed premises, the entrance sensor configured to detect entry of a person through the entry gate. An exit sensor disposed near an exit gate of the enclosed premises. The exit sensor configured to detect exit of a person through the exit gate. A control unit coupled to the entrance sensor and the exit sensor. The control unit is configured to receive an entry signal from the entrance sensor, the entry signal indicative of one person entering the store, receive an exit signal from the exit sensor, the exit signal indicative of one person exit the store, keeping a tally of the number of persons entering the store based on the entry signal, keeping a tally of the number of persons exit the store based on the exit signal, determine a difference between the number of persons entered and the number of persons exit from the enclosed premises at a predetermined time, comparing the difference with a predetermined value, wherein the predetermined value is indicative of the desired number of persons that can be present in the enclosed premises at one time, and operating the entry gate based on the comparison.

In one aspect, the system further includes a thermal imaging sensor disposed near the entry gate. The thermal imaging sensor configured to detect the body temperature of a person at the entry gate. The thermal imaging sensor coupled to the control unit, wherein the control unit is further configured to receive the body temperature from the thermal imaging sensor, and compare the received body temperature with normal body temperature, wherein the step of operating the entry gate further depend upon an outcome of the comparison of the received body temperature with the normal body temperature. The control unit can also send a notification to a staff device, the notification comprising the body temperature.

In one aspect, the system further comprises a camera near the entry gate. The camera configured to capture images of persons at the entry gate. The camera can be coupled to the control unit, wherein the control unit is further configured to receive the images from the camera; analyze the images to obtain one or more features, the one or more features comprise person wearing a facemask, distances between adjacent persons, and count of the persons; determine, based on the features, if the person at the entry gate is wearing the facemask, wherein the step of operating the entry gate further depends upon the person at the entry gate is wearing the mask.

In one aspect, the entry gate can be opened for allowing the person at the entrance to get in, wherein the entry gate is opened when the person at the entry gate is wearing the facemask and having the normal body temperature.

In one aspect, the entrance sensor is a camera The camera is configured to capture images of persons at the entry gate, the control unit further configured to receive the images from the camera; analyze the images to obtain one or more features, the one or more features comprise person wearing a facemask, distances between adjacent persons, entry of the person through the entry gate, and count of the persons; determine, based on the features, if the person at the entry gate is wearing the facemask, wherein the step of operating the entry gate further depends upon the person at the entry gate is wearing the mask.

In one aspect, the control unit is further configured to determine if the persons at the entry gate are wearing the facemask; determine distances between the adjacent persons at the entry gate; compare the determined distances with a predetermined distance value; display a waiting time to the persons at the entry gate, and issue one or more notifications based on the persons at the entry gate are wearing the facemask and the comparison of the distances. The predetermined distance value can be indicative of the minimum distance between two persons for maintaining social distancing. The notification can be an audio notification.

In one aspect, the system further comprises a plurality of cameras installed in the store. The plurality of cameras configured to capture images of persons in the store. The plurality of cameras coupled to the control unit, the control unit is further configured to receive the images from the plurality of cameras; analyze the images to obtain one or more features, the one or more features includes person wearing a facemask, distances between adjacent persons, and count of the persons; identifying, based on the one or more features, at least one person of the persons inside the store not wearing the facemask; determine, based on the one or more features, distances between the adjacent persons inside the store; comparing the distances with a predetermined distance value, and issue a notification based on the comparison. The notification can be issued when at least one of the distances is less than the predetermined distance value, the notification is an audio notification. The control unit is further configured to notify the identified person for not wearing the facemask. The control unit can also count the number of persons inside the store at the predetermined time and correlate the count with the actual number of persons inside the store for self-learning. The self-learning refers to machine learning included in the control unit.

In one aspect, disclosed is a method of automating crowd management at an enclosed premises. The method including the steps of providing an entrance sensor at an entry gate of a store, the entrance sensor configured to detect entry of a person through the entry gate; providing an exit sensor at an exit gate of the person, the exit sensor is configured to detect exit of a person through the exit gate; keeping a tally of the number of persons entering the enclosed premises and exit the enclosed premises based on signals received from the entrance sensor and the exit sensor; determining a difference between the number of persons entered and the number of persons exit from the enclosed premises at a predetermined time; comparing the difference with a first predetermined value, the first predetermined value indicative of the desired number of persons that should be present in the store at one time; providing, a plurality of cameras in the store and at the entry gate, the plurality of cameras configured to capture images of the persons inside the store and at the entry gate; analyze the images to obtain one or more features, the one or more features comprise person wearing a facemask, distances between adjacent persons, and count of the persons; identifying, based on the one or more features, at least one person of the persons inside the enclosed premises not wearing the facemask; determining, based on the one or more features, distances between the adjacent persons inside the store; comparing the distances with a second predetermined value, the second predetermined value indicative of a minimum desired distance between two persons; and operating the entry gate based on the difference between the number of persons entered and the number of persons exit from the store at the predetermined time.

In one aspect, the method further comprises providing a thermal imaging sensor near the entry gate, the thermal imaging sensor configured to detect the body temperature of a person at the entry gate; receiving the body temperature of the person at the entry gate; comparing the body temperature with a normal body temperature, wherein the step of operating the entry gate further depend upon an outcome of the comparison of the body temperature with the normal body temperature. A notification including the body temperature can be sent to the staff device.

These and other objects and advantages of the embodiments herein will become readily apparent from the following detailed description.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
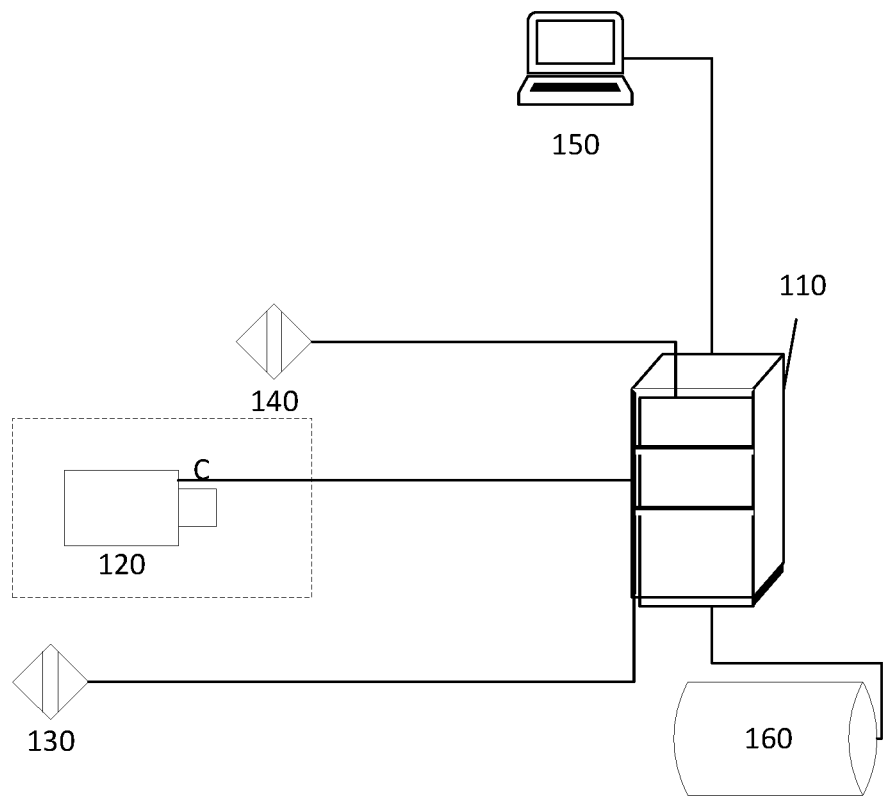
FIG. 1 is a block diagram showing the system environment according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as apparatus and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth to provide a thorough understanding of the subject innovation. It may be evident, however, that the claimed subject matter may be practiced without these specific details. In other instances, well-known structures and systems are shown in block diagram form to facilitate describing the subject innovation.

The present disclosure is directed to a system and method for automating the crowd management in an enclosed premises. The following description illustrates certain embodiments of the present invention using retail store as an enclosed premises. However, all kinds of enclosed premises wherein persons can assemble are within the scope of the present invention. Referring to FIG. 1, which is a block diagram of the system, the system includes a control unit 110 that can connect with at least one camera 120. The dotted line around the camera 120 shows the retail store, wherein the camera 120 can be deployed in the retail store. Although FIG. 1 shows only one camera in the retail store, it is, however, obvious that multiple cameras can be installed in the retail store. Perhaps, the number of cameras 120 required to be installed in the retail store may depend on the floor area and arrangement of sections in the store premises. The cameras should at least cover all the areas of the retail store where the customers are present normally for shop and billing. FIG. 1 further shows the control unit coupled to an entrance sensor 130 and an exit sensor 140. The entrance sensor 130 can be installed near the entry gate of the retail store. While the exit sensor 140 can be installed near the exit gate of the retail store. It is obvious, the retail stores can have multiple entries and exits, and in such case, each of the entry and exit can be equipped with the entrance sensor 130 and the exit sensor 140, respectively. FIG. 1 further shows the control unit 110 connected to a staff device 150. It is, however, obvious that the control unit can connect to more than one staff device. The staff device can be a laptop, a desktop, a smartphone, a tablet computer, and alike. A database 160 can connect to the control unit for storing the recordings.

The camera installed in the retail stores can be dome cameras or any other camera known to be used in an entity for security purposes. The cameras, however, can be of a high resolution that can capture high-resolution images. The high-resolution images allow features to be recognized from the captured images by the control unit. The control unit can be configured with a machine learning program to learn and extract the features from the captured images. In one case, the feature can be a person wearing a mask. In another case, the feature can be the person wearing the mask properly. Still, in another case, the feature can be a distance between two customers or between the customer and the staff member. Yet, in another case, the feature can be the count of customers in a store at a given time. The staff members can be recognized by the control unit through analysis of images, wherein the staff members can also wearing Identity card or bar codes that may be read by the control unit to identify a staff member. The control unit can be configured to combine feeds from different cameras installed in the retail store to generate a floor plan. Alternatively, a field view area can be set for each camera by the control unit. In addition to the images, the control unit can also receive a video feed from the cameras. In one case, the control unit can set the rate of capturing the images or the frames per second in the case of the video.

The entrance sensor 130 can be installed near the entrance for counting the entrants entering the retail store. The entrance sensor can be any sensor known to a skilled person for detecting a person passing-by the field of the sensor. For example, a laser-based sensor can be used, wherein the entrant passes the laser's path, results in a signal. The one signal can be equivalent to one entrant entering the store. Alternatively, a camera can also be used for counting the customers entering the retail store. The camera can be similar to the camera 120 and can extract the features of the entrants, such as the entrant is wearing a mask or not. In one exemplary embodiment, the camera can be separate, i.e. both first sensor and camera can be used at the entrance. Both the first sensor and the camera installed at the entrance can be connected to the control unit.

Additionally, a thermal imaging sensor can also be equipped at the entrance of the retail store. The thermal imaging sensor can be a part of the first sensor 130 or separate from it. The thermal sensor can be used to detect the temperature of the entrant at the entry gate. The thermal sensor, like the first sensor, can be connected to the control unit. The functioning of the thermal sensors for capturing the body temperature of a human being is known to a skilled person. Also, it is known that the thermal sensor works only up to a limited range. Therefore, care should be taken that the distance between the entrant and the thermal imaging sensor is within the range.

The exit sensor 140 shown in FIG. 1 can be deployed at an exit gate of the retail store. It is, however, obvious that the retail store can also have more than one exit gate. In such a case, each exit gate can be provided with the exit sensor. The exit sensor can be configured for detecting the customer exit from the gate. The exit sensor can be similar to the entrance sensor for counting the customers leaving the retail store. The exit sensor can connect to the control unit for keeping a count of the customer leaving the retail store. Unlike the entrance, the exit can only have a sensor to keep a tally of the customers leaving the store.

The control unit 110 controls the functioning of the different components of the system disclosed herein. As explained above, the control unit can receive feed from the cameras installed in the retail store and at the entrance of the retail store. The control unit can then analyze the feed to identify one or more features. The control unit can also receive a signal from the entrance sensor installed at the entrance. Based on the signal, the control unit can keep a count of the customers entering the retail store. Similarly, the control unit can also receive a signal from the exit sensor, and based on the signal, the control unit can keep a count of the customers leaving the retail store. The control unit can keep a tally of the customers entering and leaving the retail store. The control unit can also receive the temperature reading from the thermal imaging sensor installed at the entrance. The control unit can perform one or more steps of method discloses herein based on the above inputs. In one case, the control unit can control the opening and closing of the entry gates of the retail store. In one case, if the actual number of customers inside the store is lesser than the allowed number, then the control unit can open the gate to allow a limited number of customers to enter the store. In one case, if a temperature captured of the entrant is feverish, the control unit may not allow the gate to be opened. Similarly, the gate may not be opened if the entrant is not wearing the facemask. Besides controlling the gate, the control unit may also send notification of an event i.e. customer is not wearing the mask, or the customer is feverish. To send the notification, the control unit can be connected to the staff device for sending the notification to the staff, and a speaker for broadcasting an audio notification to the customers both inside the store and waiting at the entrance. Additionally, the control unit can also connect to a display installed at the entrance for displaying the waiting time.

Figure 2:
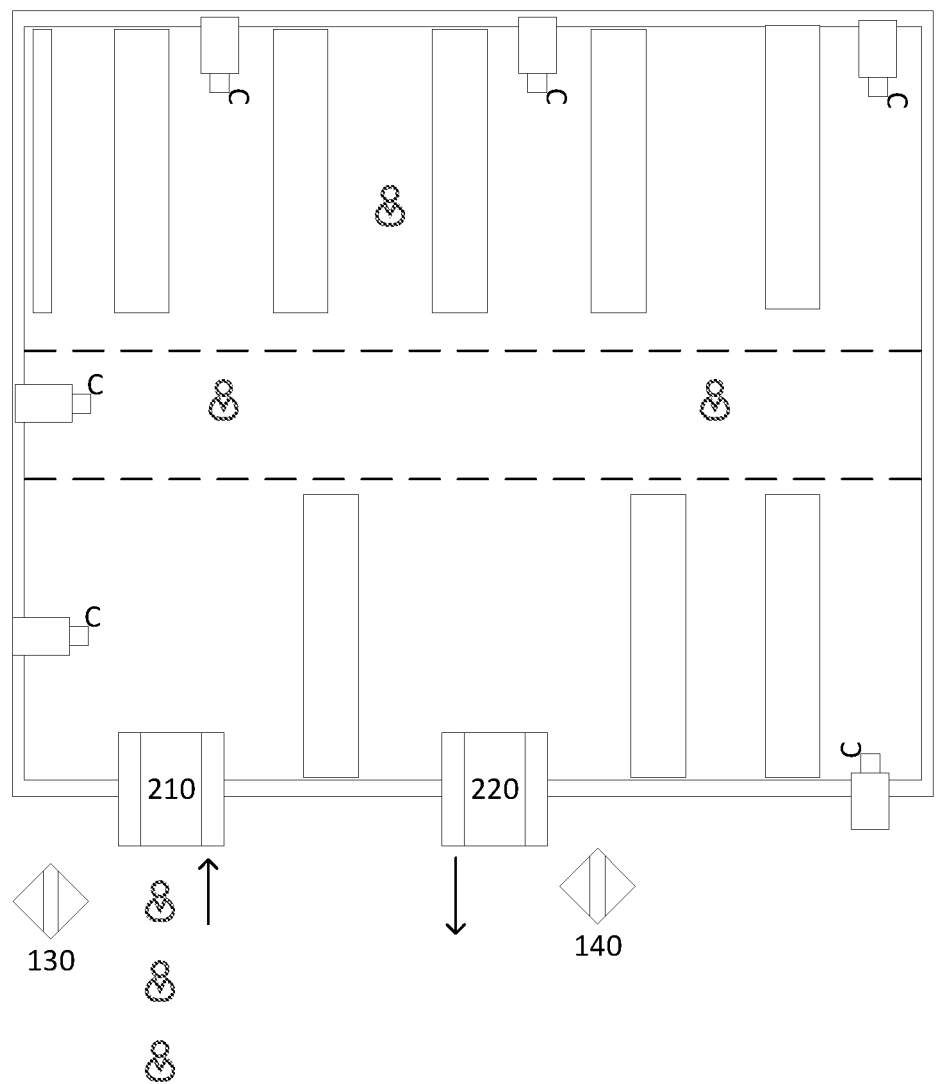
FIG. 2 is a floor plan of an exemplary retail store showing the cameras and sensors installed in the retail store, according to an exemplary embodiment of the present invention.

FIG. 2 display an example floor plan of a retail state showing the organization of the store and arrangement of racks. As can be seen in FIG. 2, the retail store is shown to be divided into the number of sections (the dotted line shows the sections). Each section is shown to be having racks for storing the goods to be sold. The racks for goods are arranged side-by-side and space is provided between the racks for the movement of the customers. Several cameras can be seen installed covering the floor area of the store. Each section can be provided with a camera to capture the movement of the customers in that section. Additionally, more than one camera can be used to capture the depth information. The arrangement of the cameras can be planned to cover the areas of the store having movement of the customers. Additionally, speakers can be installed at different locations in the store to broadcast audio warnings and notifications to both the customers and the staff. The store shown is having one entrance 210 and one exit gate 220. The entrance and exit are shown separately. Customers in the queue can be seen in front of the store for their turn to enter the store. A LED display can be positioned at the entrance of the store. Also, a speaker can be deployed near the entrance for broadcasting audio warnings and notification to the entrants. It is to be noted that the FIG. 2 shows only one example of the floor plan of the retail store, the actual retail stores can have a distinct floor plan having multiple sections, and the section can have distinct arrangement racks.

Figure 3:
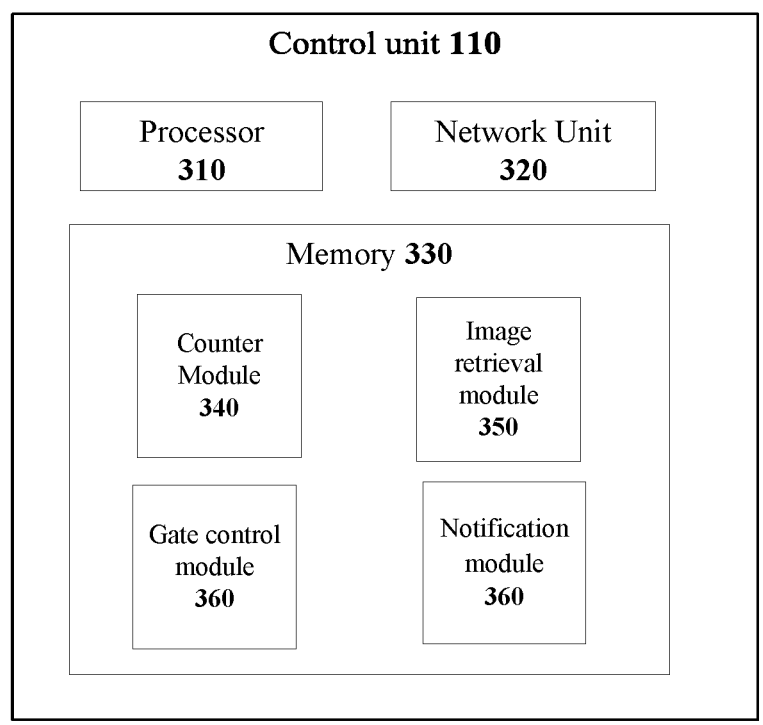
FIG. 3 is a system diagram showing the control unit, according to an exemplary embodiment of the present invention.

FIG. 3 shows an embodiment of the control unit 110 having a processor 310, a networking unit 320, and memory 330. The processor can be any microprocessor known to a skilled person for processing a set of instructions stored in a memory. For example, known are Intel processors and AMD processors. A memory stores a set of instructions which when executed by the processor causes the processor to perform one or more steps of the method disclosed herein. The networking unit allows the cameras, the first sensor, and the second sensor to be connected to the control unit. The one or more cameras, disclosed herein, can be connected directly to the control unit. Alternatively, the cameras can be connected via a wireless network or wired network. As shown in FIG. 3, the memory can include a counter module 340, an image retrieval module 350, a gate control module 360, and a notification module 360. The counter module when executed by the processor causes the processor to determine the number of customers in the store at a given time. The image retrieval module when executed by the processor causes the processor to receive and analyze the feed from the cameras for determining one or more features. The gate control module when executed by the processor, cause the processor, to control the opening and closing of the gate. The notification module when executed by the processor causes the processor to send notifications to the customers and the staff.

Figure 4:
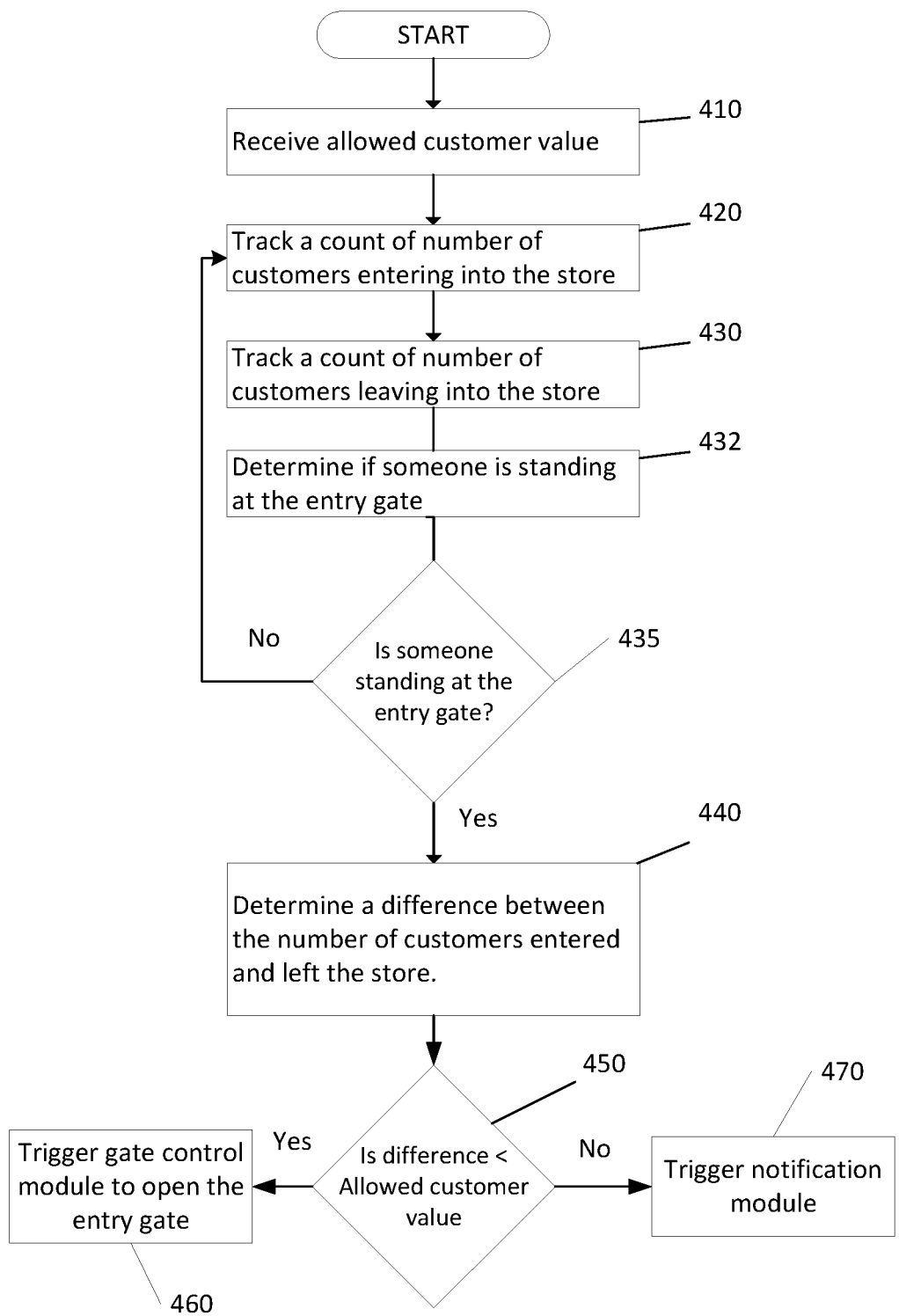
FIG. 4 is a flow chart showing an embodiment of a counter module, according to the present invention.

FIG. 4 is a flowchart showing an embodiment of the counter module 340 for crowd management in the retail store. The counter module can receive a value indicative of the allowed number of customers in the retail store at one time, at step 410. This value can be set by the staff at the time of opening the store. Additionally, this value can be adjusted by the staff through the staff device. Alternatively, the value can be determined by the control unit in near real-time based on inputs received by the control unit. The counter module can receive a signal from the entrance senor and count the number of customers entering the store, at step 420. The counter module can also receive the signal from the exit sensor and track the number of customers leaving the store, at step 430. The counter module can also determine if a person is standing at an entry gate and wishing to go inside the enclosed premises. In case of retail store, a customer wishing to enter the store. The counter module can determine if someone, such as a customer, is standing at the entry gate, at step 432. A decision is made by the counter module, at step 435, if someone is standing at the entry gate. The counter module can also keep a tally of the customers in the store at a given time based on the difference between the customers entered and the number of customers left the store In case, a customer is present at the entry gate, the counter module can determine the number of customers in the store, at step 440. A decision can be made by the counter module, at step 450, whether the customers present in the store at a given time is less than the pre-set value of the allowed number of customers. If the difference is less than the pre-set value, the control unit can trigger the gate control module to open the entry gate, at step 460, for allowing the customer to get in. Otherwise, if the difference is not less than the pre-set value, the control unit can trigger the notification module. The notification module can display a waiting time at the display. It is to be understood that the step of determining the difference between number of customers entered and left the store, at step 440, is shown in FIG. 4 after the steps 432 and 434 i.e. if someone is standing at the entry gate. However, it is obvious, that the step 440 can be performed before the step 432, without departing from the scope of the present invention. For example, staff may want to know the number of customers in the store at a given time. The counter module can determine the number of customers, at step 440 however no one is standing at the entry gate.

Figure 5:
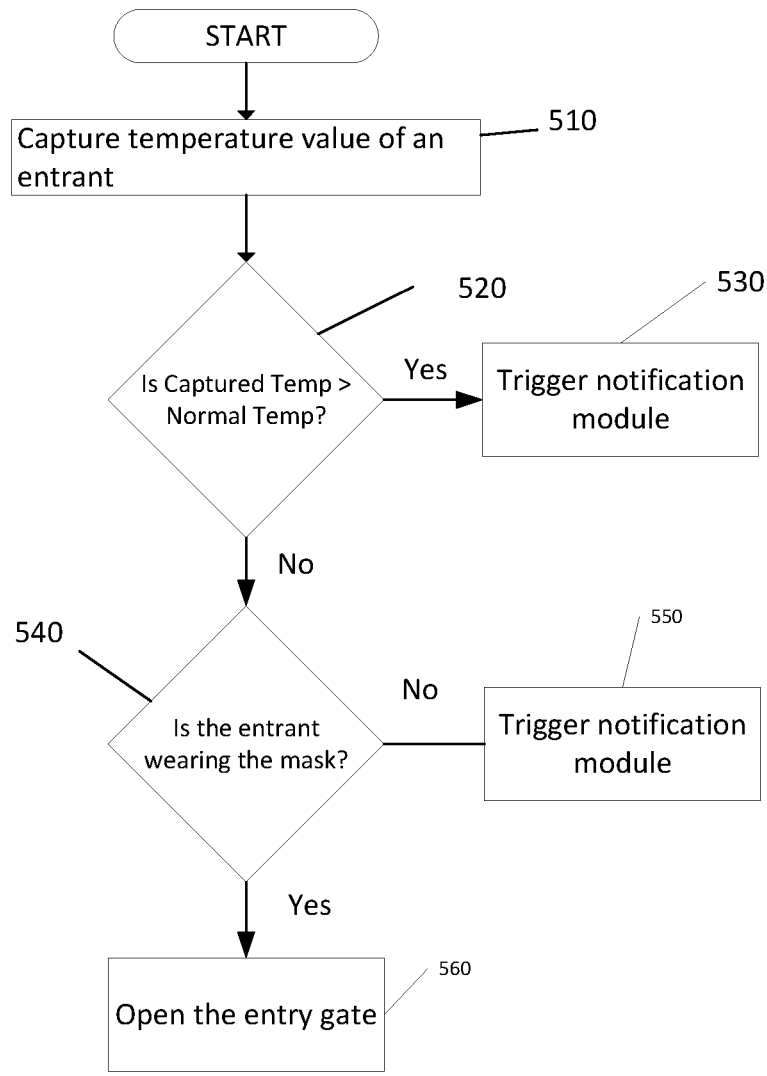
FIG. 5 is a flow chart showing an embodiment of a gate control module, according to the present invention.

The gate control module can control the opening and closing of the entry gates. Before opening the gates, the gate control module can perform a set of precautionary steps as shown in FIG. 5. The gate control module can receive the temperature of an entrant, at step 510. The temperature can be obtained by the thermal imaging sensor installed at the entrance, as explained above. A decision can be made by the gate control module, at step 520, if the captured temperature of the entrant is more than the normal body temperature. If the captured temperature is more than the normal temperature, the gate control module can trigger the notification module, at step 530. If the entrant is not feverish, the gate control module can further check, at step 540, if the entrant is wearing a facemask or not. In case, the entrant is not wearing the facemask, or the facemask is not properly worn, the gate control module can trigger the notification module, at step 550. If the entrant is wearing the facemask, the gate control module can open the entry gate for allowing the entrant to enter the retail store, at step 560. The notification module at step 530 can send a notification at the entrance, maybe as an audio message, that the customer is not allowed to enter because of fever. At step 550, the notification module can send a notification through the speaker that the customer should wear the mask before entering the gate. In both above cases, the notification module can also send the notification to the staff device that an entrant is not wearing the facemask or entrant is feverish.

Figure 6:
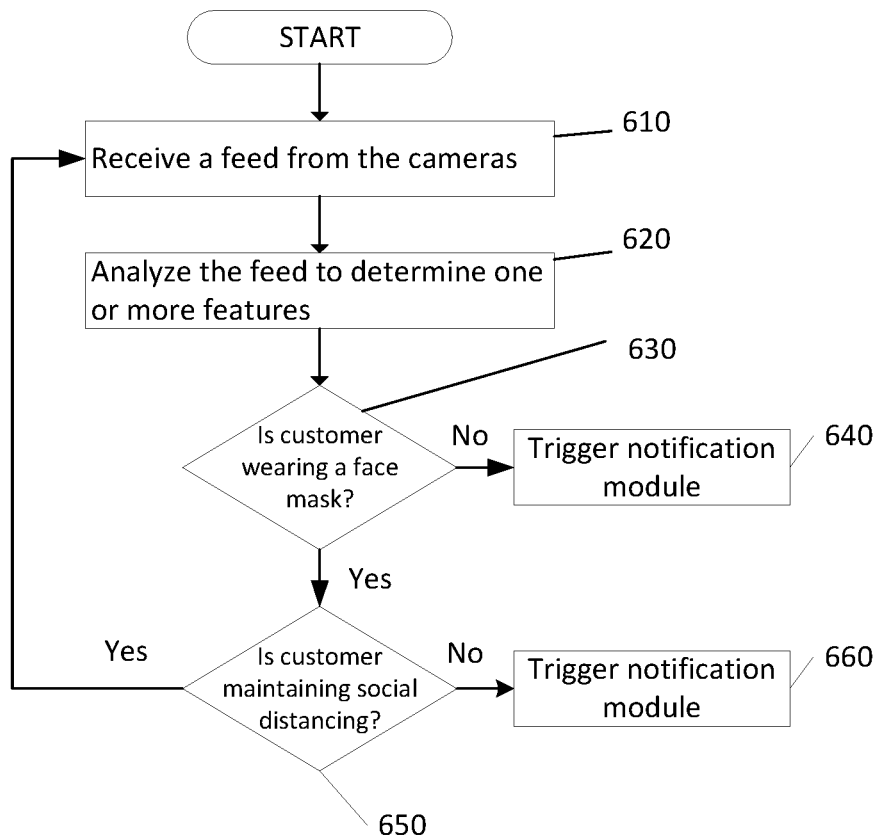
FIG. 6 is a flow chart showing an embodiment of an image retrieval module, according to the present invention.
Figure 7:
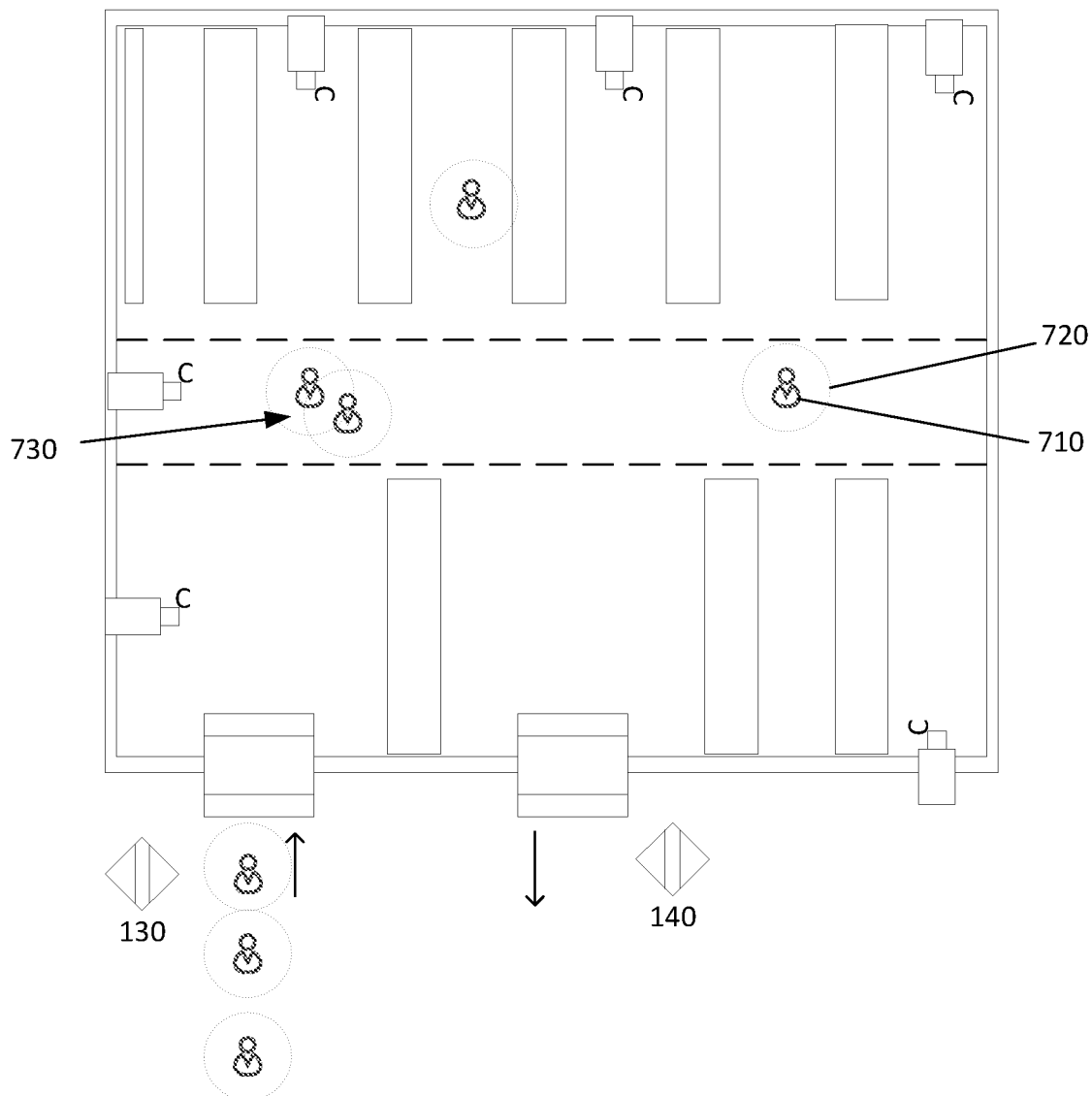
FIG. 7 is the floor plan showing a virtual perimeter mark around the customers, according to an exemplary embodiment of the present invention.

An embodiment of the image retrieval module 350 is shown in FIG. 6. The image retrieval module can receive feed from the cameras, wherein the feed can be images or video, at step 610. The image retrieval module can analyze the feed based on the image recognition algorithm and machine learning algorithms to derive one or more features, at step 620. The one or more features can include a customer wearing a facemask, or a customer maintains distance from other customers. The image retrieval module can use the input from the counter module for self-learning and its calibration. To maintain the social distance between customers within the store and also the customers waiting for their turn outside the store, the image retrieval module can set a virtual perimeter around each customer. FIG. 7 shows the floor of the retail store wherein the customers 710 is having a perimeter 720 shown by a dashed circle around the customer. In case, a customer breaches the perimeter of another customer, as shown in FIG. 7, wherein two customers 730 are within each other's parameter, the image retrieval module can trigger a warning. The image retrieval module can determine if the customers are wearing the facemask, at step 630. If any customer is not wearing the mask, the image retrieval module can trigger the notification module, at step 640. The notification module through the speaker installed nearby the customer can send an audio warning to the customer to wear the mask. The notification can also be sent to the staff device about the customer not wearing the facemask. If all the customers are wearing the mask, the image retrieval module can then determine if the social distancing is maintained, at step 650. If any customer has been in close proximity to another customer, the image retrieval module can trigger the notification module, at step 660. The notification module can send the warning by a speaker installed nearby to the customers for maintaining social distancing. If all is well within the store, the image retrieval module can continue monitoring the retail store for crowd management.

In one exemplary embodiment, the image retrieval module can also determine the type of mask worn by the customer. For example, the image retrieval module can differentiate between a surgical facemask and a N-95 facemask. Based on recognizing the type of facemask, a customer can be allowed in the store. For example, minimum standards for a facemask can be prescribed by the healthcare department. The image retrieval module can be programmed to identify the facemask worn by the customer and check its specifications. Therefore, a medical professionals entering an indoor space without the proper mask (e.g. N95) might generate a notification.

Figure 8:
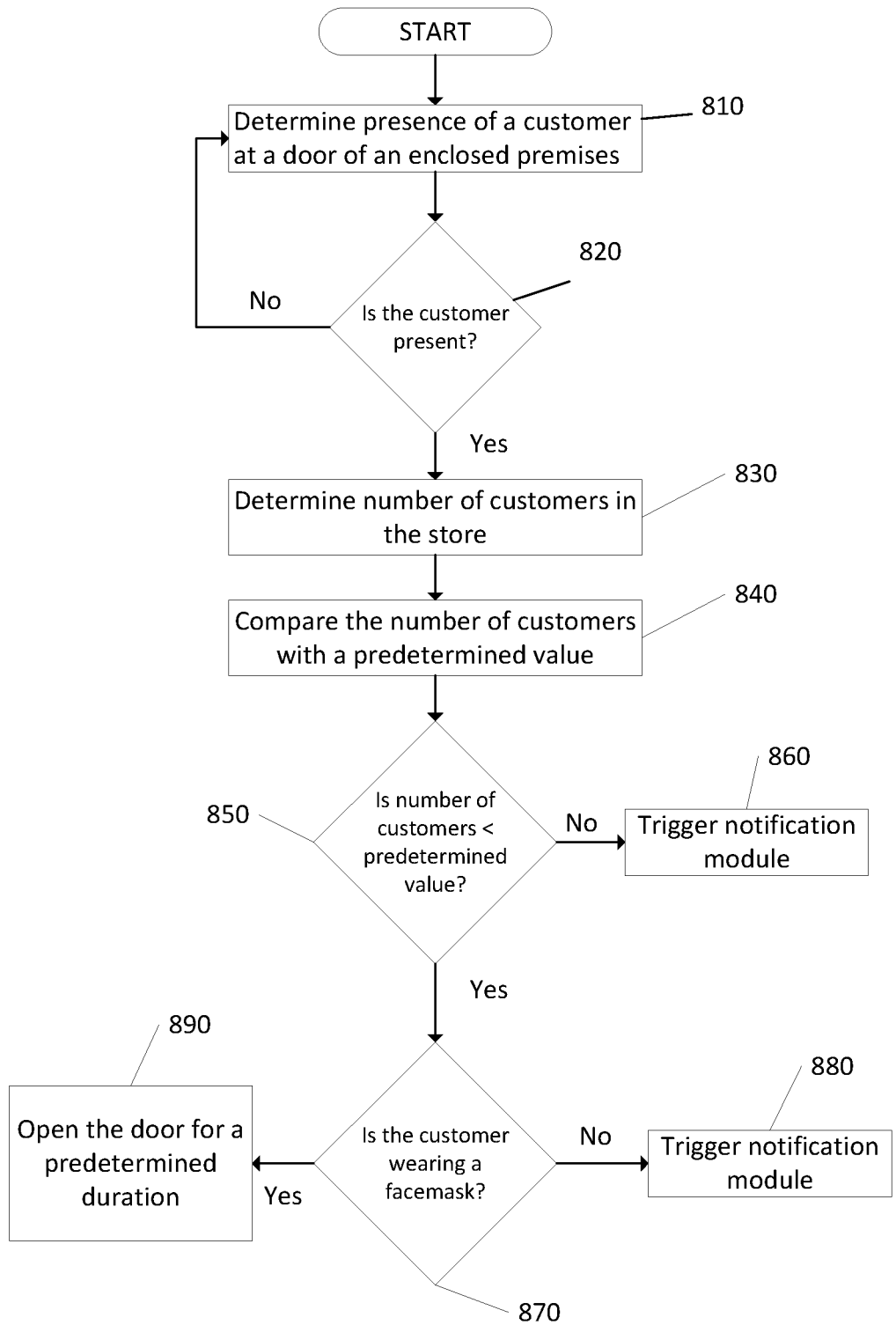
FIG. 8 is a flow chart showing a method for controlling entry to an enclosed premises, according to an exemplary embodiment of the present invention.

FIG. 8 illustrates a method for controlling entry to an enclosed premises, such as a retail store. The method includes determining presence of a customer at door of the enclosed premises, at step 810. The door is an entry gate for the enclosed premises. The presence of the customer can be checked, at step 820. If the customer is present at the door, the control unit can determine the number of customers in the enclosed premises, at step 830. Thereafter, the control unit can compare the number of the customers with a predetermined value, at step 840. The predetermined value can be pre-set in the control unit and can be based on the maximum number of customers that should be present in the enclosed premises at a given time. The comparison can be made at step 850. If the number of customers is not less than the predetermined value, notification module can be triggered, at step 860. If the number of customers is less than the predetermined value, the control unit can then determine if the customer is wearing a facemask, at step 870. If the customer is not wearing the facemask, the control unit can trigger the notification module, at step 880. If the customer is wearing the facemask, the door can be opened for a predetermined duration, at step 890. The door can be closed again after the predetermined duration. The predetermined duration can be the duration in which one customer can enter the enclosed premises.

The system disclosed herein is advantageous by regulating the entry gate of a retail store, particularly, the opening and closing of the gate. The system may only allow a limited number of customers to enter the retail store, and thereafter, automatically closes the gate. Alternatively, the system can open the gate only for a limited number of customers at a time. The system may not open the entry gate for a customer if the customer is not wearing the mask or not wearing the mask properly or having a fever. A message can be broadcast to the customer that the entry is not allowed because he is not wearing the mask. In case of high fever, the message can be that entry not allowed due to fever. The control unit can also be connected to a staff device. A notification can also be sent to a staff device that the customer not wearing the mask, or not wearing the mask properly, or is having a fever. The notification to the staff ensures that the staff is informed about the situation and appropriate action can be taken by the staff to control a situation, such as a customer not willing to wear the mask.

Additionally, the customers at the entry gate can also be tracked by the system disclosed herein, the customers can be tracked if they are maintaining proper distance among them and wearing the masks. In case, any lack of organization is realized by the system, a message can be broadcast to the customers by the system. For, example more than 10 customers may not be allowed to wait outside the store. A display can also be provided at the entry gate, wherein the display is connected to the system. The display can be an LED display and the system can display a message to the customers waiting outside the store. In one case, the message can be the approximate waiting time for the opening of the gates again and if how many customers can enter the store at one time.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A system for crowd management at an enclosed premise, the system comprising:
    an entrance sensor positioned at an entry gate of an enclosed premises, the entrance sensor configured to detect entry of a person through the entry gate;
    an exit sensor positioned near an exit gate of the enclosed premises, wherein the exit sensor configured to detect exit of a person through the exit gate;
    a thermal imaging sensor and a speaker positioned at the entry gate, the thermal imaging sensor configured to detect body temperature of a person at the entry gate, the thermal imaging sensor, the entrance sensor, and the exit sensor coupled to a control unit, the control unit configured to:
        receive an entry signal from the entrance sensor, the entry signal indicative of one person entering the enclosed premises,
        receive an exit signal from the exit sensor, the exit signal indicative of one person exit the enclosed premises,
        keep a tally of number of persons entering the enclosed premises based on the entry signal,
        keep a tally of number of persons exit the enclosed premises based on the exit signal,
        determine a difference between the number of persons entered and the number of persons exit from the enclosed premises at a predetermined time,
        compare the difference with a value indicative of desired numbers of persons that should be present inside the enclosed premises at one time,
        receive the body temperature,
        compare the body temperature with a normal body temperature,
        wherein the entry gate is kept blocked when the body temperature is higher than the normal body temperature, and
        broadcast, through the speaker at the entry gate, an audio message informing that the person cannot enter because of the higher body temperature.

2. The system of claim 1, wherein the entrance sensor is a camera, the camera configured to capture images of persons at the entry gate, the control unit further configured to:
    receive the images from the camera;
    analyze the images to obtain features, the features comprise person wearing a facemask, distance between adjacent persons, person entering through the entry gate, and count of the persons at the entry gate at a predetermined time, wherein the count of persons at the entry gate is proportional to the persons captured in the images;
    determine, based on the features, that the person at the entry gate is wearing a facemask;
    broadcast, through the speaker, an audio alert message to alert the person at the entry gate, to wear the facemask;
    keep the entry gate closed when the person at the entry gate is not wearing the facemask;
    determine, based on the features, distances between adjacent persons at the entry gate;
    compare the determined distances with a predetermined distance value, the predetermined distance value indicative of a desired distance between two persons;
    upon comparison, broadcast, through the speaker, when at least one value of the determined distances is less than the predetermined distance value, an audio alert to maintain at least the predetermined distance value.

3. The system of claim 1, wherein the system further comprises a camera positioned at the entry gate, the camera configured to capture images of persons at the entry gate, the camera coupled to the control unit, the control unit further configured to:
    receive the images from the camera;
    analyze the images to obtain features, the features comprise person wearing a facemask, distance between adjacent persons, and count of the persons at the entry gate at a predetermined time, wherein the count of persons at the entry gate is proportional to the persons captured in the images;
    determine, based on the features, if the person at the entry gate is wearing a facemask;
    broadcast, through the speaker, an audio message alerting the person at the entry gate to wear the facemask;
    keep the entry gate closed when the person at the entry gate is not wearing the facemask;
    determine, based on the features, distances between adjacent persons at the entry gate;
    compare the determined distances with a predetermined distance value, the predetermined distance value indicative of a desired distance between two persons;
    upon comparison, broadcast, through the speaker, when at least one value of the determined distances is less than the predetermined distance value, an audio alert to maintain at least the predetermined distance value.

4. The system of claim 3, wherein the control unit further configured to open the entry gate for allowing the person at the entry gate to get in when the person at the entry gate is wearing the facemask and having the normal body temperature.

5. The system of claim 3, wherein the system further comprises a display positioned near the entry gate, the control unit is further configured to:
    present, at the display, a waiting time for the opening of the entry gate, a number of persons that can enter, and a maximum number of persons allowed at the entry gate.

6. The system of claim 1, wherein the control unit is further configured to send a notification to a staff device when the body temperature is higher than the normal body temperature, the notification comprising the body temperature.

7. The system of claim 1, wherein the system further comprises:
    a plurality of cameras installed in the enclosed premises, the plurality of cameras configured to capture images of persons in the enclosed premises, the plurality of cameras coupled to the control unit;

a plurality of speakers installed in different locations of the enclosed premises, the plurality of speakers coupled to the control unit, the control unit further configured to:

receive the images from the plurality of cameras;

analyze the images to obtain features, the features comprise person wearing a facemask, distances between adjacent persons, and count of the persons inside the enclosed premises;

identify, based on the features, at least one person of the persons inside the enclosed premises not wearing the facemask;

upon identification, identify a premise's speaker of the plurality of speakers nearby the at least one person not wearing the facemask;

upon identifying the premise's speaker, broadcasting, through the premise's speaker, an audio alert for wearing the facemask;

determine, based on the features, distances between adjacent persons inside the enclosed premises;

identify at least one pair of persons of the adjacent persons having the distances less than a predetermined value, the predetermined value indicative of a minimum desired distance between two persons;

upon identification of the at least one pair of persons, identifying a premise's speaker of the plurality of speakers near the at least one pair of persons; and broadcasting, through the premise's speaker near the at least one pair of persons, an audio alert to maintain the minimum the desired distance between two persons.

8. The system of claim 7, wherein the control unit is further configured to:

identifying one or more staff members by reading identity cards worn by the one or more staff members;

count, based on the features, the number of persons inside the enclosed premises at the predetermined time; and correlate the count with the difference between the number of persons entered and the number of persons exit from the enclosed premises as determined by the entrance sensor and the exit sensor, for machine learning and calibration.

9. A method for controlling entry into an enclosed premise, the method comprises:

detecting, by a control unit, presence of a person at an entry gate of the enclosed premises;

upon detecting the presence of the person at the entry gate, determining, by the control unit using a first sensor installed at the entry gate and a second sensor installed at an exit gate, number of persons in the enclosed premise, wherein first sensor is configured to detect an entry of a person in the enclosed premises, the exit sensor is configured to detect an exit of a person from the enclosed premises, the control unit configured to keep a tally of number of persons enter and exit from the enclosed premises;

comparing the number of persons in the enclosed premise with a predetermined value, the predetermined value based on a maximum number of persons that can be present in the enclosed premises at a given time;

upon comparing the number of persons with the predetermined value, recognizing by the control unit using a camera installed at the entry gate, a facemask worn by the person;

receiving, through a thermal imaging sensor positioned at the entry gate, wherein the thermal imaging sensor configured to detect a body temperature of the person at the entry gate, the body temperature;

upon receiving the body temperature, comparing, by the control unit coupled to the thermal imaging sensor, the body temperature with a normal body temperature;

wherein the entry gate is kept blocked when the body temperature is higher than the normal body temperature; and broadcasting, through a speaker positioned at the entry gate, an audio message informing that the person cannot enter because of the higher body temperature.

10. The method of claim 9, wherein the facemask is recognized by the control unit when the number of the persons is less than the predetermined value.

11. The method of claim 9, wherein the enclosed premises is a retail store.

12. The method of claim 9, wherein the number of persons in the enclosed premises is determined based on difference between the number of persons enter and exit from the enclosed premises.

13. A system for crowd management at an enclosed premise, the enclosed premises having an entry gate and an exit gate, the system comprising:

a thermal imaging sensor positioned at the entry gate, the thermal imaging sensor configured to detect body temperature of a person at the entry gate;

a speaker positioned at the entry gate; and a control unit operably coupled to the thermal imaging sensor and the speaker, wherein the control unit is configured to:

receive the body temperature, compare the body temperature with a normal body temperature, wherein the entry gate is kept blocked when the body temperature is higher than the normal body temperature, and broadcast, through the speaker, an audio message informing that the person cannot enter because of the higher body temperature.

* * * * *